US00PP25994P2

(12) United States Plant Patent
NeSmith

(10) Patent No.: US PP25,994 P2
(45) Date of Patent: Oct. 20, 2015

(54) SOUTHERN HIGHBUSH BLUEBERRY PLANT NAMED 'TH-929'

(50) Latin Name: ***Vaccinium corymbosum* L.**
Varietal Denomination: TH-929

(71) Applicant: University of Georgia Research Foundation, Inc., Athens, GA (US)

(72) Inventor: D. Scott NeSmith, Molena, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 212 days.

(21) Appl. No.: 13/998,256

(22) Filed: Oct. 15, 2013

(51) Int. Cl.
*A01H 5/08* (2006.01)

(52) U.S. Cl.
USPC ..... Plt./157

(58) Field of Classification Search
USPC ..... Plt./157
See application file for complete search history.

*Primary Examiner* — June Hwu
(74) *Attorney, Agent, or Firm* — Klarquist Sparkman, LLP

(57) ABSTRACT

The new variety 'TH-929' is provided. The new and distinct variety ripens around the second week of May in southern Georgia. The fruit of the new variety 'TH-929' are very large, firm, and have good flavor. The new variety 'TH-929' is vigorous with an estimated chilling requirement of about 500 to 550 hours at or below approximately 7° C. The asexually reproduced variety is reliably propagated vegetatively.

5 Drawing Sheets

STATEMENT REGARDING FEDERALLY-SPONSORED RESEARCH

This invention was made, in part, with U.S. Government support on behalf of U.S. Department of Agriculture, Hatch Act Grant No. GEO 01663. The U.S. Government has certain rights in this invention.

Latin name of the genus and species of the plant claimed: 'TH-929' is a southern highbush blueberry plant that is a *Vaccinium corymbosum* L.

Variety denomination: The new southern highbush blueberry plant claimed is of the variety denominated 'TH-929'.

BACKGROUND OF THE INVENTION

The present invention relates to the discovery of a new and distinct cultivar of southern highbush blueberry plant botanically known as a *Vaccinium corymbosum* L. and herein referred to as 'TH-929', as herein described and illustrated.

The new blueberry plant variety 'TH-929' was selected in Griffin, Ga. in 2005. The new variety 'TH-929' ripens around the second week of May in southern Georgia. The fruit of the new variety 'TH-929' are large and have good flavor. The new variety 'TH-929' is vigorous with an estimated chilling requirement of about 500-550 hours at or below approximately 7° C.

Pedigree and history: 'TH-929' was selected in 2005 at the Georgia Experiment Station in Griffin, Ga., originating from a cross of 'TH-622' X 'Millennia' made by Dr. D. Scott NeSmith in 2002. The female parent ('TH-622') is a non-patented breeding line, and the male parent, 'Millennia', is the subject of U.S. Plant Pat. No. 12,816. The new variety was first asexually propagated in Griffin, Ga. by softwood cuttings. Asexual propagation by softwood cuttings has also been performed in Alapaha, Ga. The selection has been tested in plantings at Alapaha and Griffin, Ga. established in Fall 2007. In 2010, the variety was entered into preliminary trials at sites in California. In 2012 'TH-929' was entered into growing trials in Peru and Mexico. The new blueberry plant variety 'TH-929' has been shown to maintain its distinguishing characteristics through successive asexual propagation by softwood cuttings in Griffin and Alapaha, Ga. Plants from softwood cuttings have been directly planted in the ground.

SUMMARY OF THE INVENTION

The new blueberry plant variety 'TH-929' has not been observed under all possible environmental conditions. The phenotype may vary somewhat with variations in environment and cultural practices such as temperature and light intensity without, however, any variance in genotype.

The following traits have been repeatedly observed in Alapaha and Griffin Ga., and are determined to be the unique characteristics of the new blueberry plant variety 'TH-929':

1. Very large berry size;
2. Excellent berry flavor;
3. Excellent fruit firmness.

The new variety 'TH-929' can be compared to the southern highbush blueberry varieties 'Star' (the subject of U.S. Plant Pat. No. 10,675), and 'Camellia' (the subject of U.S. Plant Pat. No. 18,151).

Comparison: The selection ripens after the early variety 'Star' in south and middle Georgia, but several days before 'Camellia'. 'TH-929' has very large, firm berries with good flavor as compared to standards in Griffin and Alapaha over a 5-year period (Tables 1 and 2). Table 3 depicts berry weight, firmness and Brix for 'TH-929' as compared to several southern highbush blueberry cultivars, including 'Camellia' (U.S. Plant Pat. No. 18,151), 'TH-819' (U.S. Plant Pat. No. 24,696), 'Rebel' (U.S. Plant Pat. No. 18,138), 'Star' (U.S. Plant Pat. No. 10,675), and 'Suziblue' (U.S. Plant Pat. No. 21,167). 'TH-929' has a greater average berry firmness and Brix than all of these cultivars. It also has more protracted flowering and ripening than either 'Star' or 'Camellia'.

While the major attraction of 'TH-929' is fruit quality, the variety does have an additional favorable attribute. Preliminary trials in regions of low latitude have indicated that 'TH-929' has a propensity to perform well as an evergreen or ever bearing variety. These regions receive atypical (if any) "chill hours", and finding varieties that produce well in such regions is a challenge. Observations have revealed that 'TH-929' has the propensity to adapt to such conditions.

TABLE 1

5-year average ratings of some fruit and plant characteristics of 'TH-929' and southern highbush standard cultivars 'Camellia' and 'Star' from (2009-2013 in field test plots at Alapaha, GA. Rating scales are based on a 1 to 10 score, with 1 being the least desirable and 10 being the most desirable. A value of 6-7 is generally considered to be the minimum acceptable rating for a commercial cultivar. These plants were established in Fall 2007.

| | Alapaha location | | |
|---|---|---|---|
| Attribute | 'Star' | 'Camellia' | 'TH-929' |
| Berry size | 7.6 ± 0.2 | 8.9 ± 0.2 | 8.5 ± 0.2 |
| Berry scar | 7.0 ± 0.1 | 7.2 ± 0.2 | 7.3 ± 0.1 |
| Berry color | 7.1 ± 0.1 | 8.7 ± 0.2 | 8.4 ± 0.2 |
| Berry firmness | 7.2 ± 0.1 | 7.2 ± 0.1 | 7.6 ± 0.1 |
| Berry flavor | 7.0 ± 0.1 | 7.8 ± 0.1 | 7.4 ± 0.2 |
| Cropping | 4.7 ± 1.7 | 5.4 ± 0.3 | 5.1 ± 0.8 |
| Plant vigor | 6.3 ± 0.2 | 9.8 ± 0.2 | 8.1 ± 0.3 |
| Date of 50% flowering | March 3 | March 11 | March 8 |
| Date of 50% ripening | May 8 | May 15 | May 16 |
| Fruit development period (days) | 66.3 ± 6.1 | 65.3 ± 4.9 | 69.0 ± 5.7 |

TABLE 2

5-year average ratings of some fruit and plant characteristics of 'TH-929' and southern highbush standard cultivars 'Camellia' and 'Star' (2009-2013) in field test plots at Griffin, GA. Rating scales are based on a 1 to 10 score, with 1 being the least desirable and 10 being the most desirable. A value of 6-7 is generally considered to be the minimum acceptable rating for a commercial cultivar. These plants were established in Fall 2007.

| | Griffin location | | |
|---|---|---|---|
| Attribute | 'Star' | 'Camellia' | 'TH-929' |
| Berry size | 7.4 ± 0.2 | 8.6 ± 0.2 | 8.8 ± 0.1 |
| Berry scar | 6.9 ± 0.1 | 7.0 ± 0.1 | 7.3 ± 0.2 |
| Berry color | 7.1 ± 0.1 | 7.9 ± 0.2 | 8.3 ± 0.2 |
| Berry firmness | 7.2 ± 0.1 | 7.2 ± 0.1 | 7.3 ± 0.2 |
| Berry flavor | 7.1 ± 0.1 | 7.4 ± 0.2 | 7.3 ± 0.2 |
| Cropping | 6.8± 1.1 | 7.9 ± 0.2 | 5.4 ± 0.4 |
| Plant vigor | 8.5 ± 0.3 | 9.8 ± 0.1 | 7.5 ± 0.3 |
| Date of 50% flowering | March 13 | March 25 | March 19 |
| Date of 50% ripening | May 25 | May 31 | May 30 |
| Fruit development period (days) | 73.3 ± 10.4 | 67.3 ± 4.8 | 71.7 ± 7.2 |

TABLE 3

Berry weight, firmness, and Brix for several southern highbush blueberry cultivers and 'TH-929' grown in Griffin, GA during 2013.

| Selection or cultivar | Berry weight (g) | Berry firmness (g/mm) | Berry Brix (%) |
|---|---|---|---|
| 'Camellia' | 2.56 | 150 | 13.3 |
| 'TH-819' | 1.73 | 150 | 13.7 |
| 'Rebel' | 2.52 | 192 | 12.5 |
| 'Star' | 1.79 | 191 | 13.5 |
| 'Suziblue' | 2.54 | 190 | 13.7 |
| 'TH-929' | 2.30 | 209 | 14.0 |

BRIEF DESCRIPTION OF THE FIGURES

The accompanying photographic illustration shows typical specimens in full color of the foliage and fruit of the new variety 'TH-929'. The colors are as nearly true as is reasonably possible in a color representation of this type.

BOTANICAL DESCRIPTION

Figure 1:
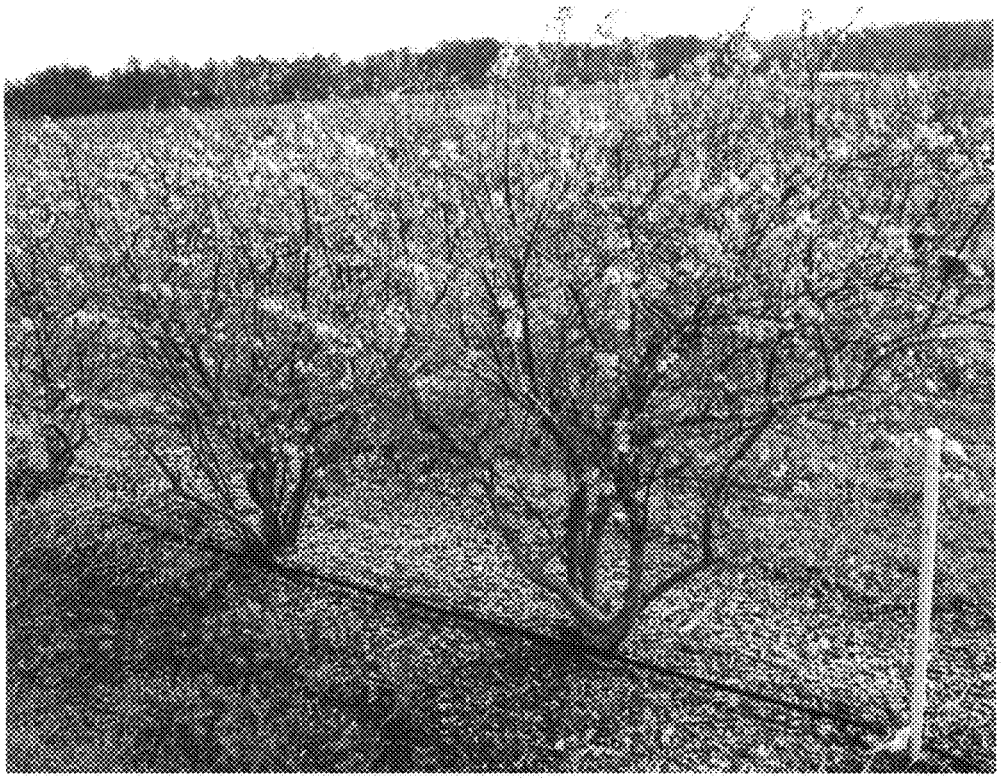
FIG. 1 is a photograph of plants of the new variety 'TH-929' during flowering in Griffin Ga.
Figure 2:
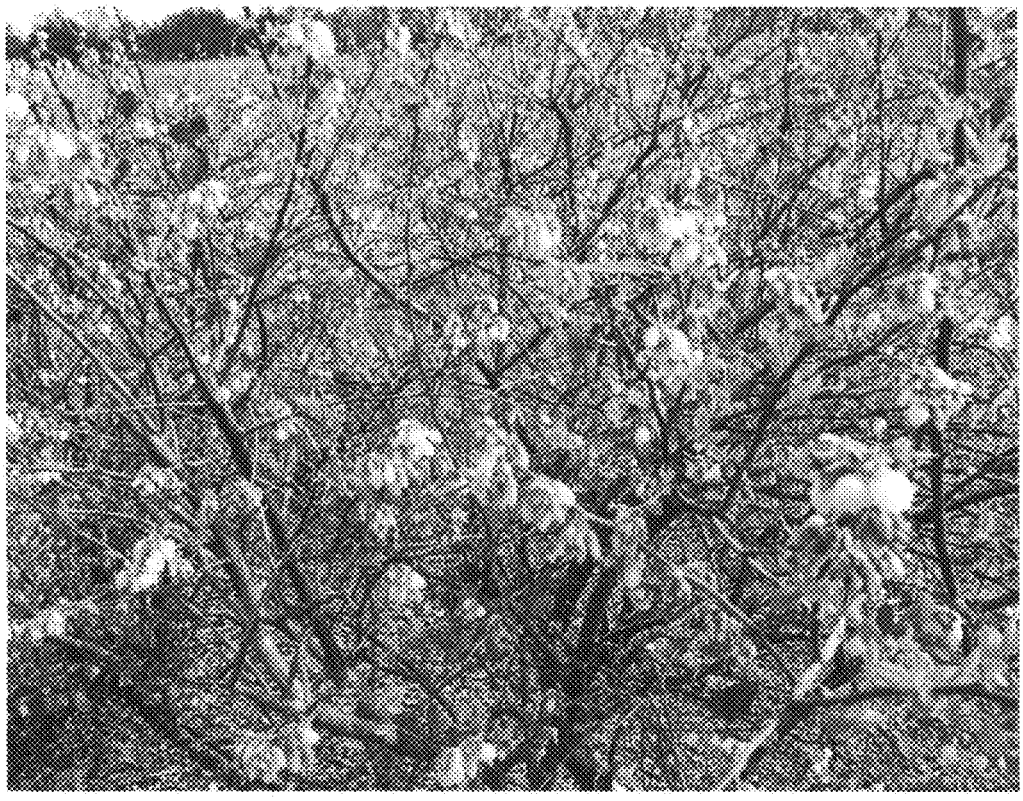
FIG. 2 is a close up photograph of one plant of the new variety 'TH-929' during flowering in Griffin Ga.
Figure 3:
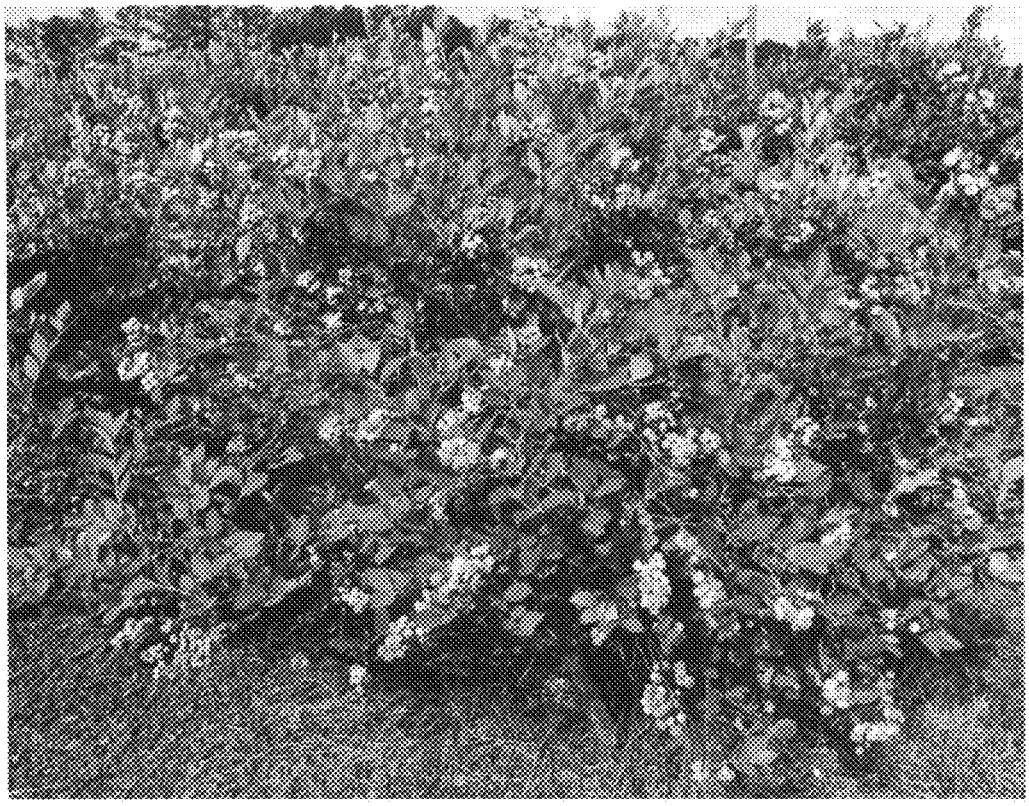
FIG. 3 is a photograph of plants of the new variety 'TH-929' during fruit ripening in Griffin, Ga.
Figure 4:
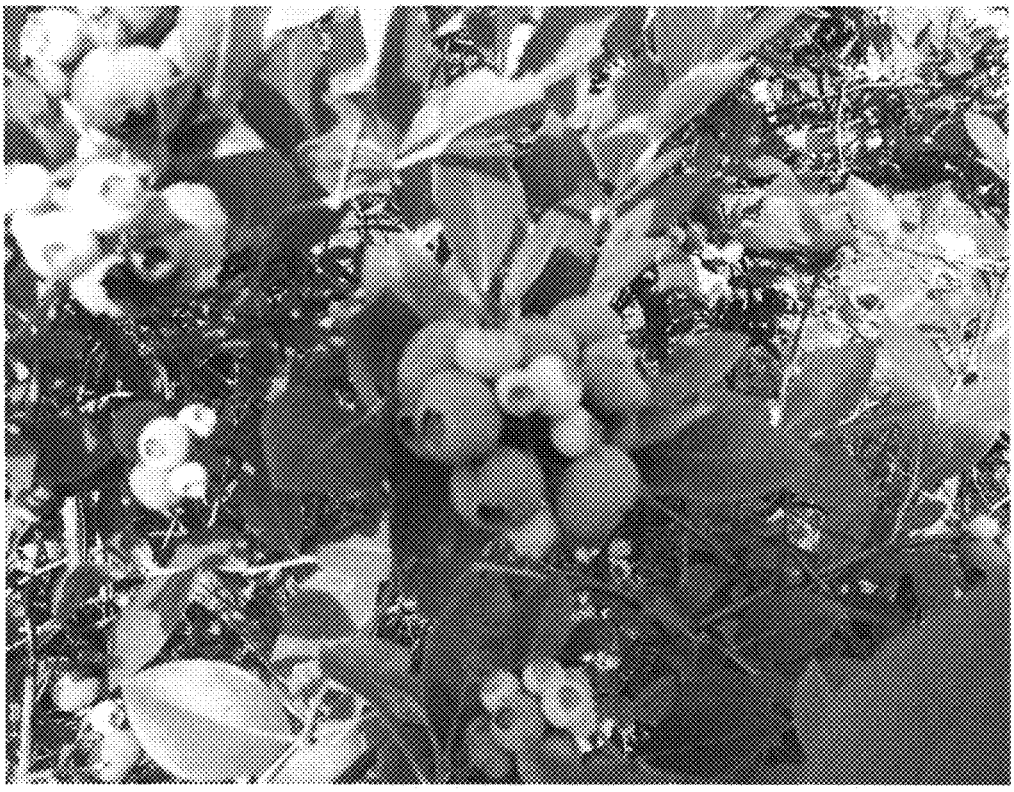
FIG. 4 is a close up photograph of a portion of a plant with fruit of the new variety 'TH-929'.
Figure 5:
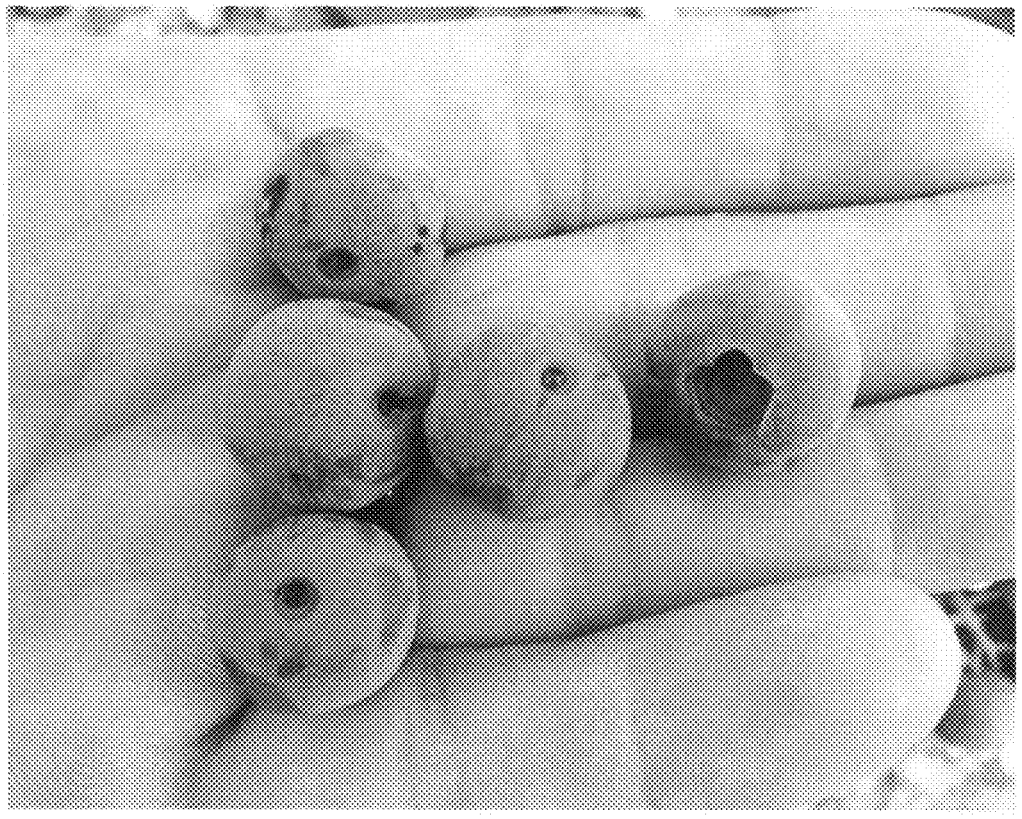
FIG. 5 is a close up photograph of several individual berries from a plant of the 'TH-929' variety.

Throughout this specification, color names beginning with a small letter signify that the name of that color, as used in common speech, is aptly descriptive. Color names beginning with a capital letter designate values based upon The R.H.S. Colour Chart, 5$^{th}$ edition published by The Royal Horticultural Society, London, England.

The following is a detailed description of the botanical and pomological characteristics of the new variety 'TH-929'. Where dimensions, sizes, colors, and other characteristics are given, it is to be understood that such characteristics are approximations and averages set forth as accurately as practicable. The descriptions reported herein are largely from specimen plants grown in Alapaha and Griffin, Ga., with supplemental irrigation. Plants were about 4 to about 7 years old.

PLANT

Size: 1.2 to 1.5 m tall by about 4 years of age. Plants grown under highly productive soil and fertility conditions have exceeded 1.5 m tall in 4 years. The plant crown, or base, is narrow, typically 20 to 25 cm in diameter. Upper portion of plant canopy exceeds 1.5 m in diameter by 4 to 5 years.

Growth habit: Semi-spreading to semi-upright, with 3 to 5 main canes arising from the crown and multiple branching of shoots from those canes beginning 10 cm or less above ground.

Growth: Highly vigorous.

Productivity: Medium to high yield, averaging 8 to 12 lbs of fruit per plant each year for plants 4 years and older grown under well fertilized and irrigated field conditions.

Hardiness: Similar to other southern highbush cultivars such as 'Star' and 'Camellia'.

Chilling requirement: 500-550 hours of temperatures at or below about 7° C. (about 45° F.) to induce normal leafing and flowering during the spring under conventional production systems. The chill requirement is less that the female parent 'TH-622,' but more than the male parent 'Millenia'. 'TH-929' has shown a propensity for evergreen production with little or no chilling when grown under lower latitudes.

Leafing: Plants tend to break sufficient leaf buds simultaneously with, or shortly after, anthesis.

Canes:
*Diameter.*—30 to 40 mm for base of canes that are about 4 years old and older. 15 to 25 mm in first major branch diameter. 10 to 15 mm in about 2 year old wood. 5 to 10 mm in current season wood.
*Color.*—Grey RHS 201B to Grey RHS 201C for base of canes that are about 4 years old and older. Grey-green RHS 197A to Grey RHS 201B in first major branch. Yellow-green RHS 144C to Greyed-orange RHA 167B in about 2 year old wood. Yellow-green RHS 144C to Yellow-green RHS 144D in current season wood.
Fruiting wood: Moderate number of twigs 15 to 25 cm in length, with internode lengths of 10-15 mm common.
Disease resistance: No exceptional disease resistance or susceptibility observed; similar to southern highbush 'Star' and 'Camellia.'

FOLIAGE

Leaf color: Healthy mature leaves.
*Top side.*—Green RHS N138A to Green RHS N138B and glaucous and smooth.
*Under side.*—Green RHS 138D.
Leaf arrangement: Alternate, simple.
Leaf shape: Elliptic to oblanceolate.
Leaf margins: Nearly entire with occasional slight sinuate edge.
Leaf venation: Pinnate, slightly reticulated.
Leaf apices: Broadly acuminate.
Leaf bases: Acute.
Leaf dimensions:
*Length.*—50 to 60 mm.
*Width.*—30 to 35mm.
Petioles: Small.
*Length.*—3.0 to 3.5 mm.
*Width.*—1.5 to 2.0 mm.
*Color.*—Yellow-green RHS 145A.

FLOWERS

Date of 50% anthesis: March 5 to March 12 (5 year average) in southeast Georgia.
Flower shape: Urceolate.
Flower bud number: Very high, averaging 5 to 8 buds per fruiting shoot.
Flowers per cluster: 6 to 9.
Flower fragrance: None.
Corolla:
*Color.*—White RHS 155C (open flower).
*Length.*—8.0 to 9.0 mm.
*Width.*—6.5 to 7.5 mm.
*Aperture width.*—3.0 to 3.5 mm.
Flower peduncle:
*Length.*—10 to 12 mm.
*Color.—Green RHS* 139D with Red-purple RHS 58A streaking visible in cooler weather.
Flower pedicle:
*Length.*—3.0 to 4.0 mm.
*Color.*—Green RHS 138C.
Calyx (with sepals):
*Diameter.*—7.0 to 8.0 mm.
*Color.*—Sepals, Green RHS 138C; Calyx body Green RHS 138B.
Stamen:
*Length.*—7.5 to 8.0 mm.
*Number per flower.*—10.
*Filament color.*—Yellow-green RHS 145C.
Style:
*Length.*—9.0 to 10.0 mm.
*Color.*—Yellow-green RHS 145B.
Pistil:
*Length.*—11.0 to 12.0 mm.
*Ovary color* (*exterior*).—Green RHS 138C.
Anther:
*Length.*—4.5 to 5.0 mm.
*Number.*—10.
*Color.*—Greyed-Orange RHS 165B.
Pollen:
*Abundance.*—Medium to high.
*Color.*—Yellow-white RHS 158A.
Self-compatibility: The cultivar has demonstrated a moderate degree of self-compatibility.

FRUIT

Date of 50% maturity: May 10 to 18 (5 year average) in southeast Georgia.
Fruit development period: 60 to 80 days.
Berry color:
*With wax.*—Violet-blue RHS 97B to Blue RHS 100D.
*With wax removed.*—Black RHS 202A.
Berry surface wax abundance: High.
Berry flesh color: Green-white RHS 157B.
Berry weight:
*First harvest.*—2.0 g to 3.0 g.
*Second harvest.*—1.8 g to 2.3 g.
Berry size:
*Height from calyx to scar.*—13.0 to 16.0 mm.
*Diameter.*—15.0 to 20.0 mm.
Berry shape: Semi-spherical.
Fruit stem scar: Medium, dry, no tearing at harvest.
Calyx: Depth 2.0 to 3.0 mm; width 5.0 to 8.0 mm; sepals not highly visible, slightly erect when present.
Berry firmness: Moderate to very firm.
Berry flavor and texture: Sweet, mildly acidic flavor; smooth.
Storage quality: Good to very good.
Suitability for mechanical harvesting: Not likely suited.
Uses: Can be used for fresh fruit for shipping, but also customer-pick and processing markets.

SEED

Seed abundance in fruit: Medium, with 10 to 20 fully developed seeds per berry.
Seed color: Greyed-orange RHS 165B.
Seed dry weight: 52.6 mg per 100 seeds.
Seed size: 1.5 to 2.0 mm long for fully developed seeds.

What is claimed is:

1. A new and distinct variety of southern highbush blueberry plant named 'TH-929', substantially as illustrated and described herein.

* * * * *